United States Patent [19]

Senba et al.

[11] Patent Number: 4,700,572
[45] Date of Patent: Oct. 20, 1987

[54] AUTOMATIC ULTRASONIC FLAW DETECTING SYSTEM

[75] Inventors: Takashi Senba; Satoru Tachikawa, both of Kanagawa, Japan

[73] Assignee: Mitsubishi Denki Kabushiki Kaisha, Tokyo, Japan

[21] Appl. No.: 842,458

[22] Filed: Mar. 21, 1986

[30] Foreign Application Priority Data

Apr. 3, 1985 [JP] Japan .................................. 60-70311
Apr. 3, 1985 [JP] Japan ............................. 60-49421[U]

[51] Int. Cl.$^4$ ............................................ G01N 29/04
[52] U.S. Cl. ........................................ 73/622; 73/638
[58] Field of Search .......................... 73/622, 637, 638

[56] References Cited

U.S. PATENT DOCUMENTS 4,487,072 12/1984 Livingston ............................ 73/622

FOREIGN PATENT DOCUMENTS 55-138649 10/1980 Japan .

Primary Examiner—Anthony V. Ciarlante
Attorney, Agent, or Firm—Wolf, Greenfield & Sacks

[57] ABSTRACT

An automatic ultrasonic flaw detecting system adapted to search flaws on steel pipes being continuously transferred and provide markings at the positions of flaws on the steel pipes. The system comprises a probe adapted to search flaws on the steel pipe, a holder for the probe, and a flaw pulse generation circuit adapted to generate flaw pulse signals in response to the flaw signals from the probe. A travel measurement pulse generator generates measurement pulse signals by measuring the distance which the steel pipes have travelled. A pipe and sensor detects the end of the steel pipe and generates pipe end detection signals. A flaw tracking control apparatus tracks the flaws in response to the flaw pulse signals, the measurement pulse signals and the pipe end detecting signals and generates marking control signals. A marking is provided at the position of flaws detected on the steel pipe in response to the marking control signals.

3 Claims, 13 Drawing Figures

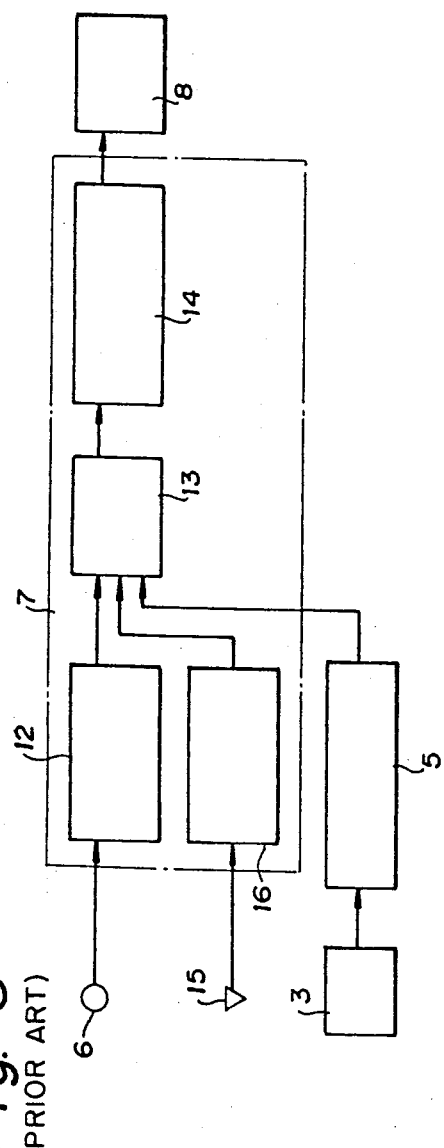
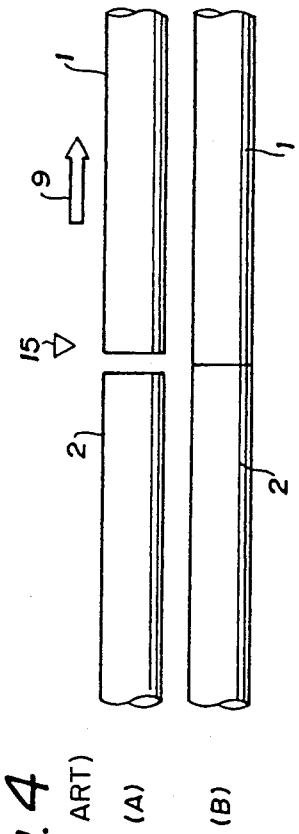
Fig. 3 (PRIOR ART)
Fig. 4 (PRIOR ART)

AUTOMATIC ULTRASONIC FLAW DETECTING SYSTEM

TECHNICAL FIELD

The present invention relates to an automatic ultrasonic flaw detecting system adapted to continuously search the positions of defects on a steel pipe and in particular to an improvement of an automatic ultrasonic flaw detecting system adapted to detect the positions of defects on a steel pipe and provide a marking representative of the positions.

PRIOR ARTS

FIG. 1 and FIG. 2 schematically show a conventional automatic ultrasonic flaw detecting system adapted to continuously search the positions of defects on a steel pipe and to provide a marking representative of said positions, and in particular such a type of automatic ultrasonic flaw detecting system which employs pipe end detection sensors to detect the end of a steel pipe being continuously transferred. FIG. 2 particularly illustrates a block circuit diagram of the control unit shown in FIG. 1 for tracking the defects.

In FIG. 1 are shown the steel pipe 1 being currently inspected; the steel pipe 2 to be next inspected; a probe 3 adapted to search for defects on the steel pipes 1, 2; a means 4 for holding the probe 3; a flaw pulse generation circuit 5 adapted to generate flaw pulse signals in response to the flaw signals transmitted from the probe 3; a travel measurement pulse generation unit 6 adapted to measure the distance which said steel pipes 1, 2 have travelled; a control unit 7 adapted to track the defects in response to the flaw pulse signals generated by the flaw pulse generation circuit 5 and the distance signals provided by travel measurement circuit 12 (FIG. 2); a marking unit 8 adapted to provide a marking representative of the positions of defects found on steel pipes in response to the control signals transmitted from the control unit 7; the direction of travel 9 of steel pipes; and a steel pipe end sensor 10 adapted to detect the ends of steel pipes 1, 2.

In FIG. 2 are shown, the probe 3, the flaw pulse generation circuit 5 and the marking unit 8 which are respectively shown in FIG. 1; a pipe end detection unit 11 adapted to generate detection pulse signals in response to the detection pulses transmitted from the pipe end sensor 10; a travel measurement circuit 12 adapted to count a series of pulses provided from the travel measurement pulse generation unit 6 and generate distance pulses or shift clock signals; a flaw tracking shift register 13 adapted to delay the flaw pulses by an amount of time corresponding to the distance between the pipe end sensor 10 and the marking unit 8 in response to the output pulses transmitted from the flaw pulse generation unit 5, the pipe end detection circuit 11 and the travel measurement circuit 12; and a marking timing pulse generation circuit 14 adapted to generate marking timing pulses in response to the output signals from the shift register 13; said timing pulse energizing the marking unit.

In the system according to a prior art shown in FIG. 1 and FIG. 2, when the probe 3 detects any flaw on the pipe 1 and outputs a flaw signal, the flaw pulse generation circuit 5 is caused to transmit a flaw pulse to the tracking shift register 13 in response to the flaw signal. The tracking shift register 13 in turn inputs as shift clock signals a series of travel pulses (e.g. having respectively a duration of 1 mm/pulse) provided by the travel measurement circuit 12. The register 13 is reset when the front end of a steel pipe is detected by the pipe end detection sensor 10 and the pipe end detection pulse is generated by the pipe end detection circuit 11. Simultaneously upon the register 13 being reset, shifting or tracking operation of the register is commenced and when the pipe end sensor detects the rear end of the steel pipe, the shifting operation is completed in response to the rear end detection pulse provided by the pipe end detection circuit. When the shift register 13 receives the flaw pulse during the shifting operation, the flaw data represented by the flaw pulse is sequentially shifted by the shift clock signal and delayed by the amount of time corresponding to the distance between the pipe end sensor 10 and the marking unit 8. The flaw pulse thus delayed is then caused to drive the marking unit 8 through the marking timing pulse generation circuit 14 including an amplifier. The marking unit in turn provides a marking at the position of the flaw on a steel pipe while the flaw to be marked is passing through the marking unit.

In the automatic ultrasonic flaw detecting system as described above, there has been a problem in that when a marking is to be provided at the location of a flaw at the rear end portion of a given steel pipe 1, the marking may be made at the front end portion of the next steel pipe 2 instead due to the delay in timing of the marking caused by the accumulative errors built up in the flaw pulse generation unit 5, the error in tracking of the control unit 7, timing errors of the marking unit 8, blurring of the marking paint or the like, all of which result in marking errors (in the order of within +100 mm).

FIG. 3 illustrates an automatic ultrasonic flaw detecting system according to a prior art wherein an eddy current sensor 15 adapted to monitor the continuity of composition of a steel pipe is employed as th pipe end sensor in order to detect the end of a steel pipe, this sensor being capable of distinguishing between the continuous feeding of a plurality of steel pipes and the feeding of each individual steel pipe. FIG. 3 specifically shows the block circuit diagram of a flaw tracking control unit. In FIG. 3, the same reference numerals are employed to denote components and circuits which are similar to those shown in FIG. 1 and FIG. 2.

FIG. 4 shows the feeding conditions of the steel pipes to be detected by the eddy current sensor 15, wherein FIG. 4(A) shows each of the pipes being fed independently, while FIG. 4(B) shows the steel pipes being fed continuously.

In the automatic ultrasonic flaw detecting system according to a prior art shown in FIG. 3 timing of the commencement and completion of the shifting operation of the flaw tracking shift register 13 is determined by the pulse signals provided by the eddy current detection circuit 16 in response to the pipe end detection signals from the eddy current sensor 15 or the ON signal provided when the front end of a steel pipe is detected and the OFF signal provided when the rear end of a steel pipe is detected, whereby the continuous feeding of steel pipes and the feeding of each individual steel pipe may be distinguished. Further, when the steel pipes are fed continuously, the insensitive zone wherein it is impossible to detect flaws which may exist adjacent the ends of steel pipes 1, 2 is made relatively short (in the order of 50 mm), while such insensitive zone is made longer (on the order of 100 mm) in the case of feeding individual steel pipes. This is because, in the case of continuous feeding, the flaw detection water which is the medium for detecting flaws does not penetrate into the steel pipe so that the film of flaw detection water remains stable and the insensitive zone requiring no flaw detection may be short, while in the case of individual feeding, the flaw detection water penetrates into a steel pipe so that the film of flaw detection water is unstable and the insensitive zone has to be longer.

In the eddy current detection circuit 16 according to a prior art as described above, when the next (n+1)th steel pipe 2 is fed in close proximity to the current nth steel pipe 1 (the gap between those steel pipes being on the order of 0-1.0 mm), they may be effectively detected as if they were being fed continuously. However, when some clearance exists between the steel pipes 1 and 2 (on the order of 1-400 mm), the eddy current sensor 15 detects the rear end of the nth steel pipe 1 and the front end of the next (n+1)th steel pipe. In this case, such feeding is detected as being the feeding of an individual pipe, not a continuous feeding. For such a feeding condition, the insensitive zone had to be relatively long (on the order of 100 mm).

Should the insensitive zone be made longer, the ends of the steel pipes have to be inspected once again. It is clearly preferable, therefore, that the insensitive zone be as short as possible.

SUMMARY OF THE INVENTION

Accordingly, an object of the present invention is to provide an improved automatic ultrasonic flaw detecting system which eliminates the above-mentioned drawbacks.

Another object of the present invention is to provide an automatic ultrasonic flaw detecting system wherein the timing signal for marking is corrected in respect of the flaw at the rear end portion of the steel pipe currently being inspected and marking may be correctly provided on that steel pipe without erroneously providing marking on the front end portion of the next steel pipe.

A still further object of the present invention is to provide an automatic ultrasonic flaw detecting system capable of continuously detecting steel pipes for flaws and marking the positions of such flaws, wherein in order to avoid erroneous marking on the next steel pipe due to a marking error, the pipe end of the steel pipe being examined is detected at the time of marking its rear end and the timing of such marking is corrected by provision of first and second travel measurement circuits, first and second shift registers for tracking, first and second switching circuits adapted to respectively switch the first and second travel measurement circuits and first and second shift registers for tracking, and a switching control circuit adapted to control the first and second switching circuits.

A still further object of the present invention is to provide an automatic ultrasonic flaw detecting system wherein even if a gap (on the order of 1-400 mm) which will not cause any problem in respect of flaw detection is present between pipes, the pipe ends will be detected as if it was a continuous feeding arrangement, so that the insensitive zone may be made short (on the order of 50 mm).

A yet still further object of the present invention is to provide an automatic ultrasonic flaw detecting system adapted to detect flaws continuously on a steel pipe and to provide markings at the positions of flaws wherein an eddy current sensor, an eddy current detection circuit, a steel pipe position sensor (comprising for example a photoconductive relay) and steel pipe position detection circuits are used in combination so as to detect the rear end of the nth steel pipe and the front end of the (n+1)th steel pipe and even if a gap (on the order of 1-400 mm) is present between the nth steel pipe and the (n+1)th steel pipe, the pipes may be detected as if they were being fed continuously.

According to the present invention, since erroneous markings on steel pipes caused by errors inherent to conventional tracking control units or the like may be avoided, perfect steel pipe products may be obtained.

When steel pipes are being fed, even if they are fed continuously there may be small gaps (on the order of 1-400 mm) generated between the rear end of the nth steel pipe and the front end of the (n+1)th steel pipe, depending on the feeding conditions. However, even if such small gaps are prevent, the flaw detection water which is the medium for flaw detection will not penetrate into the interior of a steel pipe and further the film of the flaw detection water is stable, so such a condition may be taken as being one of continuous feeding. According to the present invention, the insensitive zone may be made short (on the order of 50 mm) in such a case.

BRIEF DESCRIPTION OF THE DRAWING

FIG. 3 shows an automatic ultrasonic flaw detecting system according to a prior art wherein an eddy current sensor is employed as the pipe end sensor;

FIG. 4 shows the feeding conditions of the steel pipes to be detected by the eddy current sensor as shown in FIG. 3;

DESCRIPTION OF PREFERRED EMBODIMENTS

Figure 5:
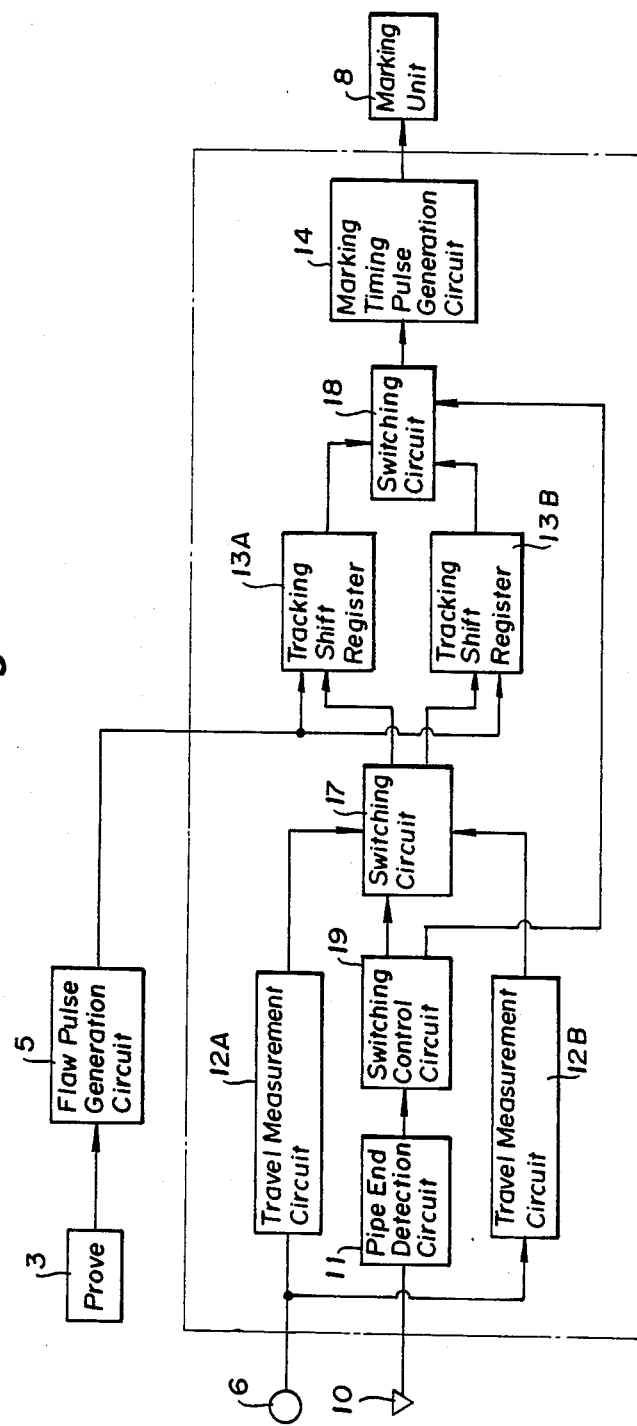
FIG. 5 is a block diagram showing a first embodiment of the present invention.

Referring now to FIG. 5 illustrating the first embodiment of the present invention, there are shown the first travel measurement circuit 12A; the second travel measurement circuit 12B to be connected in parallel to said first travel measurement circuit 12A; the first flaw tracking shift register 13A; the second flaw tracking shift register 13A to be connected in parallel to the first flaw tracking shift register 13B; the first switching circuit 17 adapted to select either the first travel measurement circuit 12A or the second travel measurement circuit 12B; the second switching circuit 18 adapted to select either the first flaw tracking shift register 13A or the second flaw tracking shift register 13B; and the switching control circuit 19 adapted to control the timing of the switching effected by the first or second switching circuits 17, 18. The other numerals in FIG. 5 denote components and circuits which are similar to those shown in FIG. 1 and FIG. 2.

Figure 2:
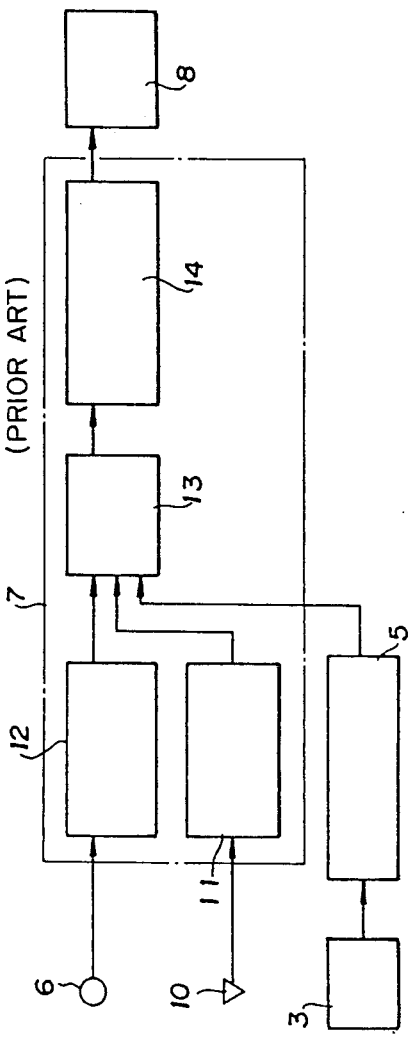

The first travel measurement circuit 12A is adapted, in the same manner as the travel measurement circuit 12 shown in FIG. 2, to count the output pulses provided by the travel measurement pulse generation unit 6 and generate a series of normal travel distance pulses in terms of 1 [mm/pulse], while the second travel measurement circuit 12B is adapted to count the output pulses provided by the travel measurement pulse generation unit 6 and generate a series of compensating travel distance pulses in the terms of $1+\Delta l$ [mm/pulse].

The switching control circuit 19 is adapted to provide switching control signals to the first and second switching circuits 17 and 18 in response to the pipe end pulses provided by the pipe end detection circuit 11 when the front end and the rear end of steel pipes are detected by the pipe end sensor 10 and to determine the timing of the switching operation of the switching circuits.

The first switching circuit 17 is adapted to output either a normal distance pulse from the first travel measurement circuit 12A or a compensating distance pulse from the second travel measurement circuit 12B in response to the switching control signals provided from the switching control circuit 19.

The first and second flaw tracking shift registers 13A and 13B input as shift clock signals the output from the switching circuit 17, that is, the distance pulse or the compensating distance pulse. When flaw pulses are generated by the flaw pulse generation circuit 5, these flaw pulses are delayed by a predetermined time or the time equivalent to the marking distance L. For example, assuming that the shift registers 13A or 13B are composed for example of flip-flops having n number of stages, the marking distance L is defined by the equation $L = n \times l$. On the other hand, assuming that the switching circuit 17 will output only compensating distance pulses, the distance L in this case is defined by the equation $L = n \times (l + \Delta l)$.

The second switching circuit 18 is adapted to output either the output signals from the first shift register 13a or the output signals from the second shift register 13B.

Figure 6:
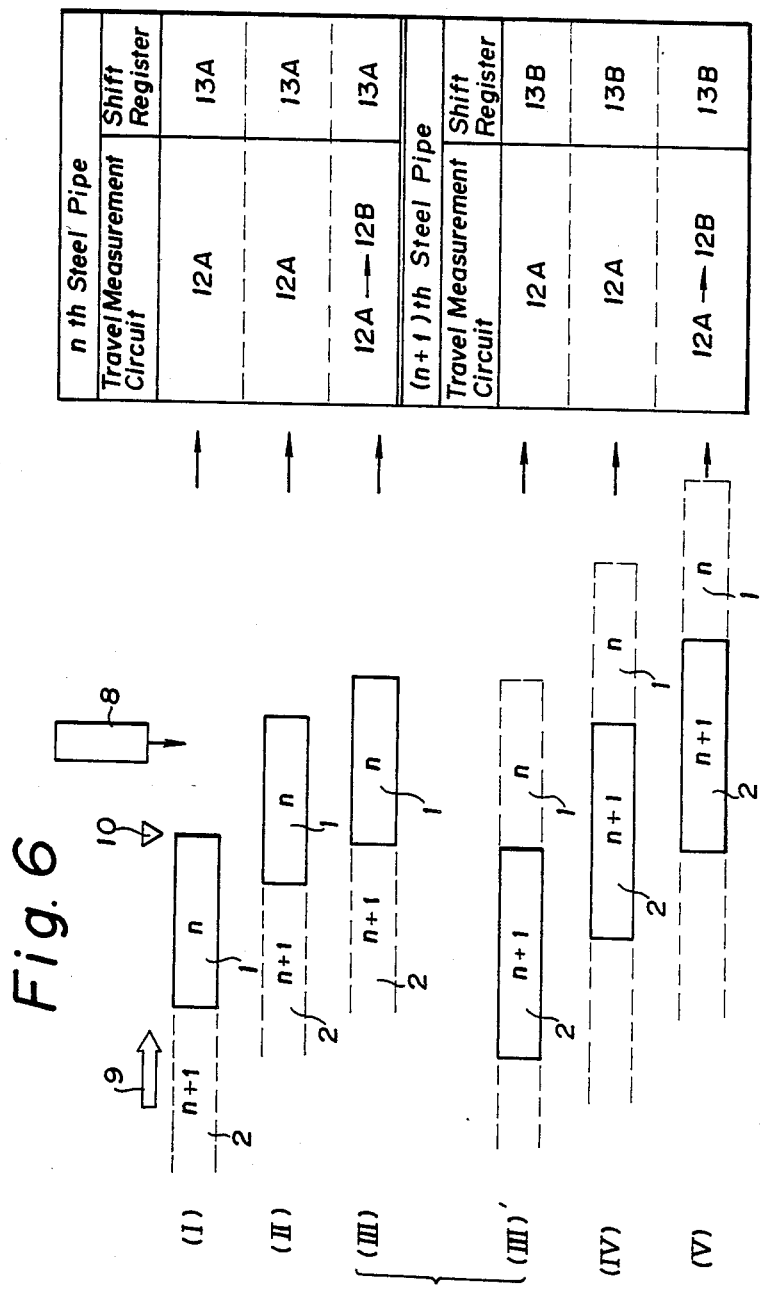
FIG. 6 shows the relationship among the steel pipes to be detected by the pipe end sensor or the feeding conditions of the nth steel pipe and the (n+1)th steel pipe, the relative travel measurement circuit to be selected by the switching circuits and the relative tracking shift register.

FIG. 6 illustrates the relationship among the steel pipes 1, 2 to be detected by the pipe end sensor 10 or the feeding condition of the nth steel pipe and the (n+1)th steel pipe, the relative travel measurement circuit 12A or 12B to be selected by the switching circuits 17 and 18 and the relative tracking shift register 13A or 13B.

Figure 7:
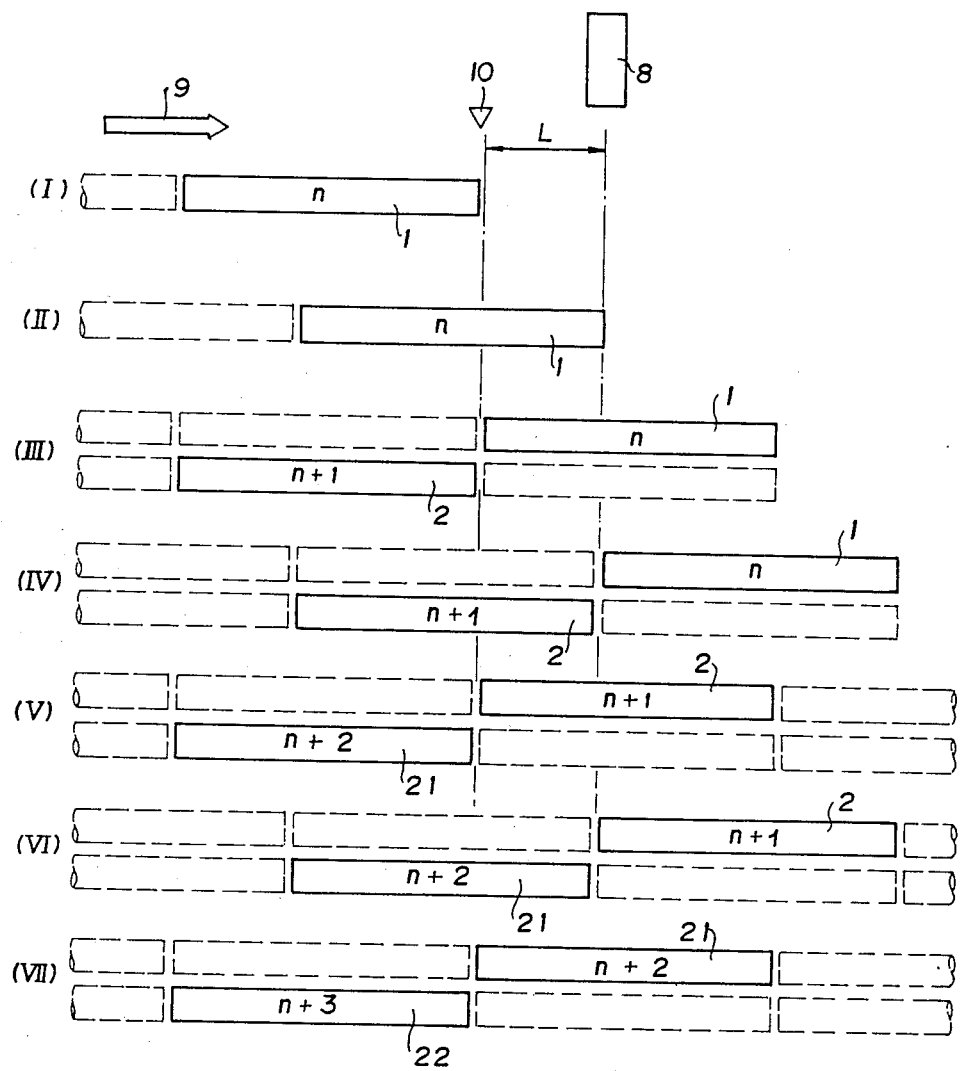
FIG. 7 shows the continuously feeding conditions of a plurality of steel pipes.
Figure 8:
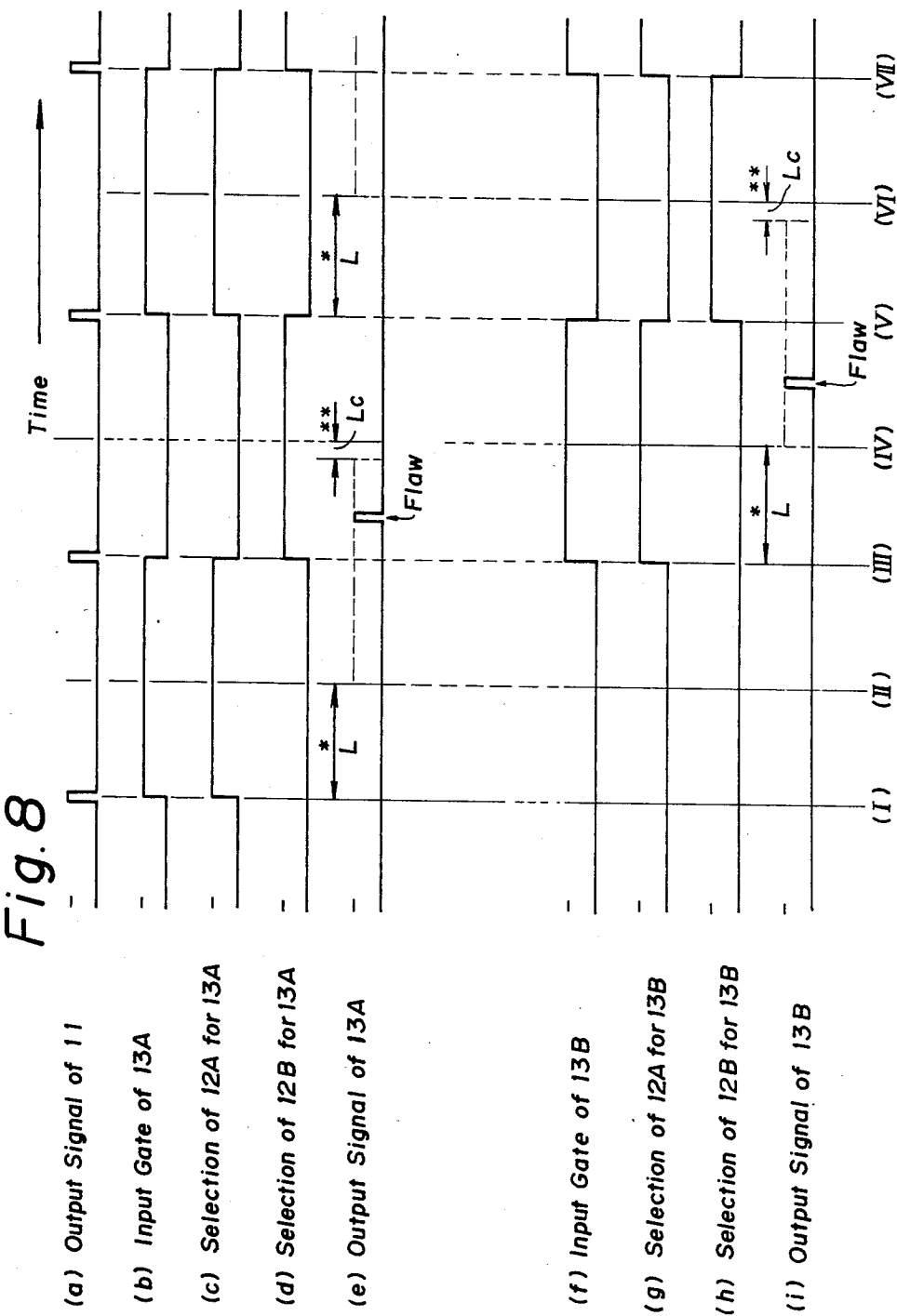
FIG. 8 is a timing chart explaining the flaw detecting system shown in FIG. 5.

FIG. 7 illustrates the continuously feeding conditions of a plurality of steel pipes n, n+1, n+2, n+3. FIG. 8 is a timing chart explaining the flaw detecting system shown in FIG. 5 as applied to the feeding conditions shown in FIG. 6 and FIG. 7 wherein FIGS. 8(b) through (e) are the timing charts relating to the shift register 13A while FIGS. 8(f) through (i) are the timing charts relating to the shift register 13B.

As shown in FIGS. 6 through 8, when the front end of the current or nth steel pipe 1 is detected by the pipe end sensor 10 (in FIG. 7 time $t_1$), the first and second switching circuits 17 and 18 are so switched as to respectively select the travel measurement circuit 12A and the tracking shift register 13A, and the travel measurement circuit 12A commences counting to generate a series of normal distance pulses in terms of 1 [mm/pulses]. On the other hand, the shift register 13A starts shifting operation, simultaneously when it is reset, in response to the distance pulses from the travel measurement circuit 12A [see FIG. 6 through FIG. 8(I)].

Then, when the rear end of the steel pipe 1 is detected by the pipe end sensor 10 (i.e., time $t_3$), the switching circuit 17 is caused to switch over the travel measurement circuit 12A to the travel measurement circuit 12B, so that the travel measurement circuit 12A stops counting and the travel measurement circuit 12B outputs the compensating distance pulse in terms of $1+\Delta l$ [mm/pulses] [see FIG. 6 through FIG. 8(III)]. Upon receiving the compensating distance pulses, the shift register 13A carries out the tracking operation. Thus, as shown in FIG. 8(e), the positions of flaws on the steel pipe 1 can be provided with markings adjacent the rear end of the steel pipe 1 at a distance shorter than the actually travelled distance by the compensated amount $L_C$ corresponding to the compensating distance pulse provided by the travel measurement circuit 12B.

Subsequently, when the front end of the next or the (n+1)th steel pipe 2 is inspected by the pipe end sensor 10, the switching circuit 17 immediately selects again the travel measurement circuit 12A while the switching circuit 18 selects the shift register 13B [see FIG. 6(III), FIG. 7 and FIG. 8(III)]. Accordingly, the travel measurement circuit 12A commences counting to generate normal distance pulses while the shift register 13B, simultaneously with being reset, receives distance pulses from the travel measurement circuit 12A to commence shifting operation.

Then, when the rear end of the steel pipe 2 is detected by the pipe end sensor 10 (that is time, $t_5$), the switching circuit 17 selects the travel measurement circuit 12B and the travel measurement circuit 12B generates the compensating distance pulse. Upon receiving the compensating distance pulses, the shift register 13B is caused to commence the tracking operation. As a result, as shown in FIG. 7(i), the positions of flaws may be provided with markings on the steel pipe 2 adjacent the rear end of the steel pipe 2 at a distance shorter than the actually travelled distance by the amount equivalent to the compensation value $L_C$, as above mentioned. Then when the front end of the (n+2)th steel pipe is detected by the pipe end sensor 10 (that is time, $t_5$), the travel measurement circuit 12a and the shift register 13a are selected. The travel measurement circuit 12A generates normal distance pulses. Simultaneously with the shift register 13A being reset again, it will receive distance pulses from the travel measurement circuit 12A and commences shifting operation.

Thus, by alternately switching the tracking shift registers 13A and 13B for the steel pipes which are being transferred continuously, the timing of marking relative to the positions of flaws is compensated at the rear end portion of the steel pipe currently being examined and thus erroneous marking of the front end portion of the next steel pipe may be prevented.

Figure 9:
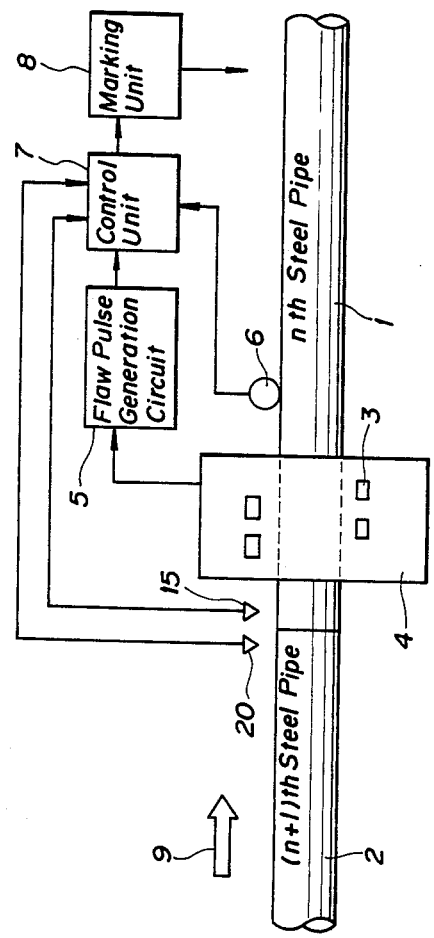
FIG. 9 is a block diagram showing a second embodiment of the present invention.

FIG. 9 illustrates the second embodiment of the present invention wherein even if a gap exists (for instance, on the order of 1–400 mm) between the steel pipes being transferred, they are detected as if they were being fed continuously and the insensitive zone may be kept as short as possible.

Figure 1:
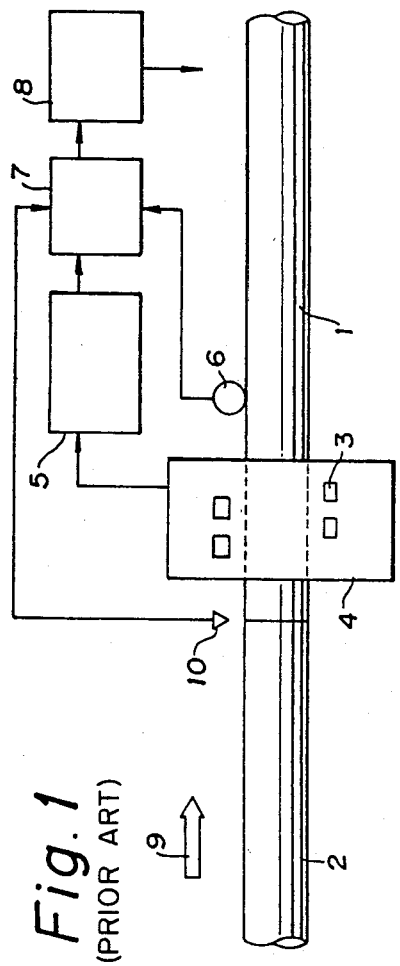
FIGS. 1 and 2 schematically show a conventional automatic ultrasonic flaw detecting system, wherein a well-known steel pipe end sensor is employed.

The detecting system shown in FIG. 9 is different from the conventional detecting system shown in FIG. 1 in that an eddy current sensor 15 and a pipe end position sensor 20 are provided.

Figure 10:
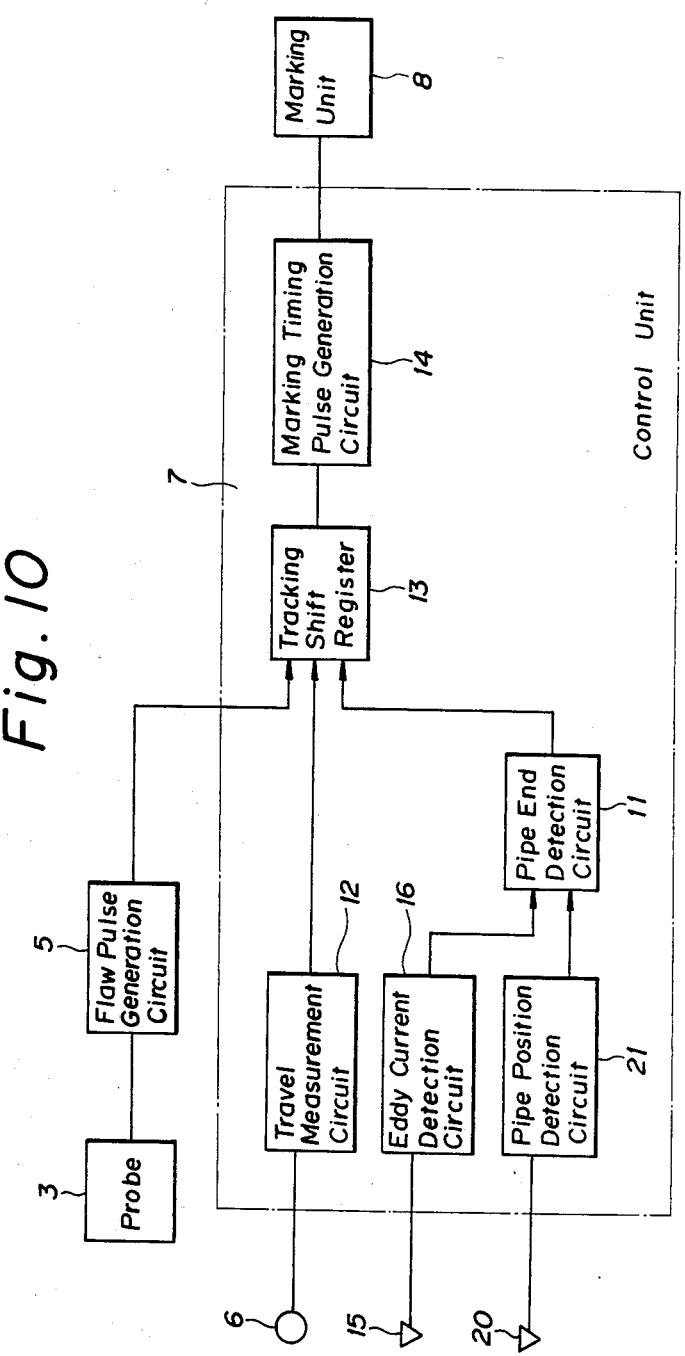
FIG. 10 is a block diagram for the flaw tracking control unit in the second embodiment of the present invention shown in FIG. 9.

FIG. 10 is the block diagram for the flaw tracking control unit 7 in the second embodiment of the present invention shown in FIG. 9. In FIG. 9, the tracking control unit 7 is comprised of a travel measurement circuit 12; a tracking shift register 13; a marking timing pulse generation circuit 14; an eddy current detection circuit 16 adapted to generate eddy current detection pulses in response to the detection signals from the eddy current sensor 15; a steel pipe position detection circuit 21 adapted to generate steel pipe position detection pulses in response to the detection signals from the steel pipe position sensor; and a pipe end detection circuit 11 adapted to output the pipe end pulses in response to the output pulses from the eddy current detection circuit 16 and the steel pipe position detection circuit 21.

The eddy current detection circuit 16 is adapted to provide ON or OFF signals while the eddy current sensor 15 monitors the continuity of the composition of the steel pipes, ON signals being provided when the continuity is maintained and OFF signals when discontinuity is detected.

The steel pipe position sensor 20 is in the form of a photo-conductive relay. The steel pipe position detection circuit 21 generates ON signals when the steel pipes are passing by the steel pipe position sensor 20 and OFF signals when no steel pipes are passing by the position sensor.

The pipe end detection circuit 11 is adapted to generate pipe end pulses in response to the change in the respective outputs of the eddy current detection circuit 16 and the steel pipe position detection circuit 21, namely the transition between ON signals and OFF signals in respect of the output of the eddy current detection circuit 16 and the transition between ON signals and OFF signals in respect of the output of the steel pipe position detection circuit 21.

FIG. 11 illustrates feeding conditions of the steel pipes and a timing chart for the operation of the detecting system shown in FIG. 10.

Figure 11A:
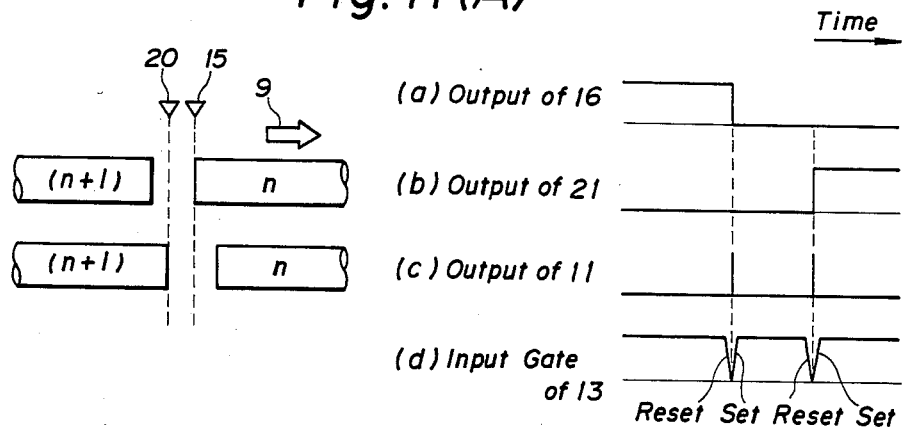
FIGS. 11a-c shows feeding conditions of the steel pipes and a timing chart for the operation of the unit shown in FIG. 10.

As shown in FIG. 11(A), when the front end of the (n+1)th steel pipe is passing by the steel pipe position sensor, or the photo-conductive relay 20, if the rear end of the preceding nth steel pipe has already passed by the eddy current sensor 15, the pipe end detection circuit 11 generates two pipe end pulses in response to the change of the respective outputs of the eddy current detection circuit 16 and the steel pipe position detection circuit 21, these pipe end pulses meaning that the steel pipes are being transferred individually.

Figure 11B:
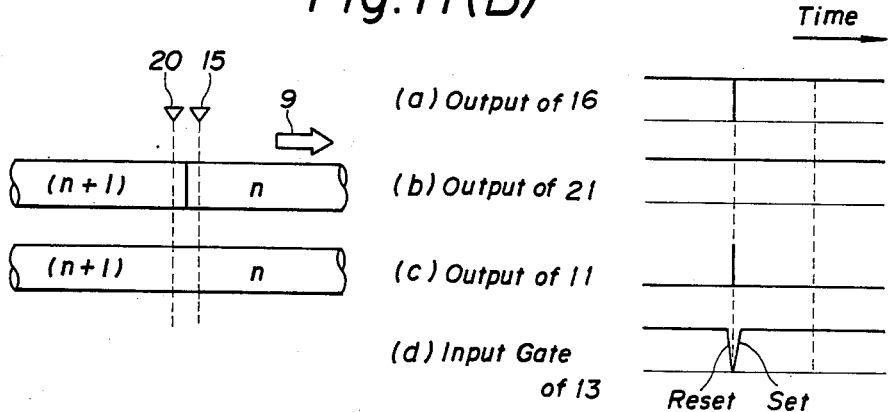

As shown in FIG. 11(B), when the front end of the (n+1)th steel pipe and the rear end of the nth steel pipe are transferred in close proximity, the eddy current sensor 15 generates a detection signal while the photo-conductive relay 20 maintains ON condition. Accordingly, the pipe end detection circuit 11 generates one pipe end pulse in response to the change in the output of the eddy current detection circuit 16 whereby said pipe end pulse indicates that the steel pipes are being continuously transferred.

Figure 11C:
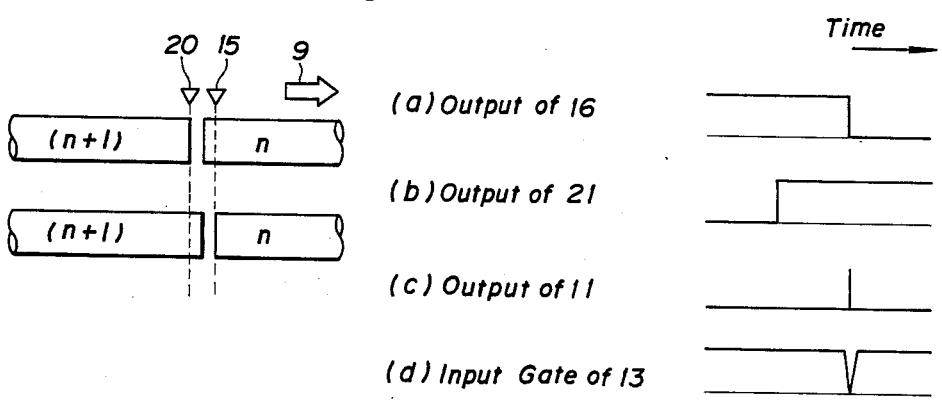

As shown in FIG. 11(C), when the front end of the (n+1)th steel pipe is passing by the photo-conductive relay 20, if the rear end of the nth steel pipe has not yet reached the eddy current sensor 15, in other words, if a small gap exists (for example on the order of 1–400 mm) between the steel pipes, the pipe end detection circuit 11 generates one pipe end pulse in response to the change in the output of the eddy current detection circuit 16, which judges that the steel pipes are being continuously transferred.

As a consequence, if the rear end of the nth steel pipe and the front end of the (n+1)th steel pipes are spaced apart by a distance greater than the distance between the eddy current sensor 15 and the steel pipe position sensor 20, the pipe end detection circuit 11 generates two pipe end pulses to indicate that the steel pipes are being individually transferred. On the other hand, if the distance between the steel pipes is shorter than the distance between the eddy current sensor and the steel pipe position sensor, the pipe end detection circuit generates one pipe end pulse to show that the steel pipes are being continuously transferred.

It is preferable that the distance between the eddy current sensor 15 and the steel pipe position sensor 20 may be adjustably set so as to judge the feeding conditions of steel pipes in accordance with the sizes of the steel pipes and the transferring speed.

We claim:

1. An automatic ultrasonic flaw detecting system adapted to search flaws on steel pipes being continuously transferred and provide markings at the positions of flaws on said steel pipes, comprising:
   (a) a probe adapted to search flaws on a steel pipe;
   (b) a means for holding said probe;
   (c) a flaw pulse generation circuit adapted to generate flaw pulse signals in response to the flaw signals from said probe;
   (d) a travel measurement pulse generator adapted to generate measurement pulse signals by measuring the distance which said steel pipes have travelled;
   (e) a pipe end sensor adapted to detect the end of said steel pipe and generate pipe end detection signals;
   (f) a flaw tracking control means adapted to track the flaws in response to said flaw pulse signals, said measurement pulse signals and said pipe end detection signals and generate marking control signals; and
   (g) a means adapted to provide a marking at the position of flaws detected on said steel pipe in response to said marking control signals;
   said flaw tracking control means further comprising:
   (a) a first travel measurement circuit adapted to count said measurement pulse signals and generate normal distance pulse signals;
   (b) a second travel measurement circuit adapted to count said measurement pulse signals and generate compensating distance pulse signals;
   (c) a pipe end detection circuit adapted to generate pipe end pulse signals in response to said pipe end detection signals;
   (d) a switching control circuit adapted to generate switching control signals in response to said pipe end pulse signals;
   (e) a first tracking shift register adapted to delay said flaw pulse signals by a predetermined time in response to said normal distance pulse signals, said compensating distance pulse signals and said flaw pulse signals in order to adjust the timing of marking relative to the position of flaws on the steel pipe being currently inspected;

(f) a second tracking shift register adapted to delay said flaw pulse signals by said predetermined time in response to said normal distance pulse signals, said compensating distance pulse signals and said flaw pulse signals in order to adjust the timing of marking relative to the position of flaws on the next steel pipe following the steel pipe currently being examined;

(g) a first switching circuit adapted to select either said normal distance pulse signals or said compensating distance signals in response to said switching control signals;

(h) a second switching circuit adapted to select either of the output signals of said first or second tracking shift register in response to said switching control signals; and (i) a circuit adapted to generate the marking timing pulse signals in response to the output signals of said first or second tracking shift register so as to control said marking means based on the selection executed by said second switching circuit.

2. The automatic ultrasonic flaw detecting system as set forth in claim 1 characterized in that said first sensor is an eddy current sensor and said second sensor is a steel pipe position sensor.

3. An automatic ultrasonic flaw detection system adapted to search flaws on steel pipes being continuously transferred and provide markings at the positions of flaws on said steel pipes, comprising:

(a) a probe adapted to search flaws on a steel pipe:

(b) a means for holding said prove;

(c) a flaw pulse generation circuit adapted to generate flaw pulse signals in response to the flaw signals from said probe;

(d) a travel measurement pulse generator adapted to generate measurement pulse signals by measuring the distance which said steel pipes have traveled;

(e) a first sensor adapted to detect the end of said steel pipe and generate first pipe end detection signals;

(f) a second sensor adapted to detect the end of said steel pipe and generate second pipe end detection signals;

(g) a flaw tracking control means adapted to track the flaws in response to said flaw pulse signals, said measurement pulse signals and said first and second pipe end detection signals and generate marking control signals; and (h) a means adapted to provide a marking at the position of flaws on said steel pipe in response to said marking control signals;

said flaw tracking control means further comprising:

(a) a travel measurement circuit adapted to count said measurement pulse signals and generate distance pulse signals;

(b) a first detection circuit adapted to generate first detection pulse signals in response to said first pipe end detection signals;

(c) a second detection circuit adapted to generate second detection pulse signals in response to said second pipe end detection signals;

(d) a pipe end detection circuit adapted to generate pipe end pulse signals in response to said first detection pulse signals and said second detection pulse signals;

(e) a tracking shift register adapted to delay said flaw pulse signals by a predetermined time in response to said distance pulse signals, said flaw pulse signals and said pipe end pulse signals so as to determine the timing of marking relative to the position of flaws on said steel pipe; and (f) a circuit adapted to generate the marking timing pulse signals in response to the output signals of said tracking shift register so as to control said marking means.

* * * * *